United States Patent [19]

Partis et al.

[11] Patent Number: 5,326,907

[45] Date of Patent: Jul. 5, 1994

[54] 2-AMINOETHANESULFONIC ACID DERIVATIVES OF 3,5-DISUBSTITUTED-4-HYDROXY-PHENOLIC THIOETHERS

[75] Inventors: Richard A. Partis, Evanston; Richard A. Mueller, Glencoe, both of Ill.

[73] Assignee: G. D. Searle & Co., Chicago, Ill.

[21] Appl. No.: 993,329

[22] Filed: Dec. 18, 1992

[51] Int. Cl.$^5$ .................................... C07C 149/00
[52] U.S. Cl. ................................................ 562/44
[58] Field of Search ................. 562/44, 105; 514/617, 514/618

[56] References Cited

U.S. PATENT DOCUMENTS

| | | | |
|---|---|---|---|
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,153,803 | 5/1979 | Thiele et al. | 560/57 |
| 4,711,903 | 12/1987 | Mueller et al. | 514/381 |
| 4,755,524 | 7/1988 | Mueller et al. | 514/381 |
| 4,954,514 | 7/1990 | Kita et al. | 562/618 |

FOREIGN PATENT DOCUMENTS 0131221 1/1985 Fed. Rep. of Germany .......... C07C 149/00

OTHER PUBLICATIONS

"Inhibitors of Leukotriene Synthesis and Action," The Leukotrienes, Chemistry and Biology, pp. 163-194, (Academic Press Inc., 1984) U.S.A.
"Commentary: Prospects for the Inhibition of Leukotriene Synthesis," Biochemical Pharmacology, vol. 33, No. 4, pp. 515-521 (1984) Great Britain.
Chemotactic Factors of Inflammation, pp. 223-225, Elsevier Science Publishers B.V., 1983, Amsterdam.
"Human Biology and Immunoreactivity of Leukotrienes," Advances in Inflammation Research., vol. 6, pp. 219-225, Raven Press, New York, 1984.
"A Review of Recent Contributions on Biologically Active Products of Arachidonate Conversion," Int. J. Immunopharmac., vol. 4, No. 2, pp. 85-90, 1982, Great Britain.
"Khimiya i Khimicheskaya Tekhnologiya," vol. 20, pp. 568-574, 1977, U.S.S.R.
"Metabolites of Arachidonic Acid," Science, vol. 217, pp. 1255-1256, 1982, U.S.A.
"Leukotrienes: Mediators of Immediate Hypersensitivity Reactions and Inflammation," Science, vol. 220, pp. 568-575, (May, 1983) U.S.A.
"Enhanced Synthesis of Leukotriene B$_4$ by Colonic Mucosa in Inflammatory Bowel Disease," Gastroenterology, vol. 86, pp. 453-460, 1984, U.S.A.
"Editorial: Leukotrienes and Other Lipoxygenase Products in the Pathogenesis and Therapy of Psoriasis and Other Dermatoses," Arch Dermatol, vol. 119, pp. 541-547, 1983.

Primary Examiner—José G. Dees
Assistant Examiner—Keith MacMillan
Attorney, Agent, or Firm—Roberta L. Hastreiter; Roger A. Williams

[57] ABSTRACT

The present invention relates to compounds of the Formula I

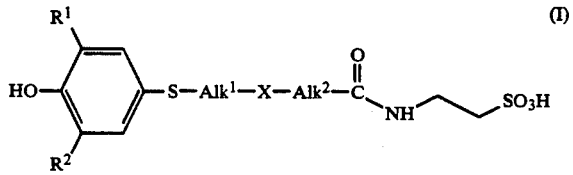

wherein $R^1$ and $R^2$ are the same or different and independently represent tert-alkyl, halogen, or phenyl; $Alk^1$ represents straight or branched chain alkylene of 2 to 10 carbon atoms which can optionally be substituted by hydroxy, provided that said hydroxy is not attached to a carbon which is adjacent to sulfur or oxygen, X represents sulfur or oxygen, and $Alk^2$ represents straight or branched chain alkylene of 1 to 4 carbon atoms; and the pharmaceutically acceptable salts thereof. These compounds are specific 5-lipoxygenase inhibitors and are useful as anti-inflammatory and anti-allergy agents and in the treatment of conditions mediated by 5-lipoxygenase.

12 Claims, No Drawings

2-AMINOETHANESULFONIC ACID DERIVATIVES OF 3,5-DISUBSTITUTED-4-HYDROXYPHENOLIC THIOETHERS

BACKGROUND OF THE INVENTION

1. Field of the Invention

The present invention relates to taurine derivatives of substituted phenolic thioethers and more particularly relates to the novel compounds of formula I which are specific 5-lipoxygenase inhibitors and are useful, for example, as anti-inflammatory and anti-allergy agents and in the treatment of diseases mediated by 5-lipoxygenase.

2. Background Information

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase pathway and are useful in the treatment of asthma, rheumatoid arthritis, psoriasis, and other allergic, hypersensitivity, and inflammatory conditions.

See Bengt Samuesson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienea, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses" *Arch Dermatol*, Vol. 119, pp 541–547 (July, 1983); Robert A. Lewis et al., "A Review of Recent Contributions on Biologically active Products of Arachidonate Conversion" *Int. J. Immunopharmac.*, Vol. 4, No. 2, pp 85–90 (1982); Michael K. Bach, *Biochemical Pharmacology*, Vol. 23, No. 4, pp 515–521 (1984); and E. L. Becker, *Chemotactic Factors of Inflammation*, pp 223–225 (Elsevier Science Publishers V. B., Amsterdam, 1983); P. Sharon, and W. F. Stenson, *Gastroenterology*, Vol. 84, 454 (1984); and Musch, M. W. et al., *Science*, Vol. 217, 1255 (1982).

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

Various thioether compounds have been described previously. For example, European Patent Application publication No. 0131221 discloses compounds of the formula

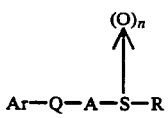

in which Ar is phenyl or phenyl substituted by one to three substituents selected from alkyl, alkenyl, alkoxy, alkylthio, alkanoyl, hydroxy, hydroxyalkyl, carboxyl, alkoxycarbonyl, carbamoyl, nitro, amino, or halogen. Q is oxygen, sulfur or an NH group; A is straight or branched chain $C_{2-8}$ alkylene which may be substituted by hydroxy or interrupted by an ethenylene or an ethinylene group; R is hydrogen or straight or branched alkyl, optionally substituted by alkoxy, hydroxyl, carboxyl, alkoxycarbonyl, or, if desired, substituted carbamoyl or amino groups; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0 without mention of any preference among the numerous possible substituents for R or substituted phenyl as Ar. In contrast to the invention disclosed in the foregoing publication, the compounds of the present invention all have a sulfur atom at the position corresponding to Q as well as having di(tertiary)-alkyl or diphenyl groups as substituents on the phenol moiety corresponding to the substituted Ar group in the above publication which, as described therein, may or may not comprise a phenol. The compounds of the present invention also have an alkyanoylaminoethanesulfonic acid substituent corresponding to the R group in the above publication. Moreover, it is noted that the compounds of the present invention have been found to possess specificity for the inhibition of 5-lipoxygenase which is an important distinctive property not attributed to the compounds in the foregoing publication. Those of ordinary skill in the art will appreciate that the compounds of formula I of this invention, including their surprising specific 5-lipoxygenase inhibitory properties, are, therefore, not specifically described in the aforementioned EPA publication No. 0131221.

U.S. Pat. No. 4,711,903 and U.S. Pat. No. 4,755,524 disclose substituted phenolic thioethers of the formula:

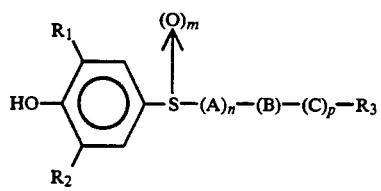

wherein: $R_1$ and $R_2$ are the same or different and independently represent tert -alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl, or a tetrazole group; m is 0 or 1, n is 2, 3 or 4 and p is 1, 2 or 3; and the pharmaceutically acceptable salts thereof. The compounds are specific inhibitors of 5-lipoxygenase and are useful in the treatment of local and systemic inflammation, allergy and hypersensitivity reactions and other disorders in which agents formed in the 5-lipoxygenase metabolic pathway are involved. In contrast to the invention disclosed in the foregoing patents, the compounds of the present invention all have —$C(O)NH(CH_2)_2SO_3H$ at the position corresponding to $R_3$ in the above patents.

U.S. Pat. Nos. 4,029,812, 4,076,841 and 4,078,084 disclose compounds of the formula

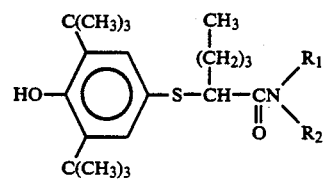

comprising 2-(3,5-di-tert-butyl-4-hydroxy-phenyl) thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., *Khimiya; Khimicheskaya Tekhnologiya*, Volume 20 , (1977), pp. 568-574. The compounds resulting from the foregoing process have the general formulas $RS(CH_2)_nX$ and $S(CH_2CH_2X)_2$ in which R is 3,5-di-tert-butyl-4-hydroxyphenyl and X represents, for example, —CXN, $NH_2$, $CH(OH)CH_2Cl$, OH, COCl and various carboxy, carboxylate and amide functions. Compounds of formula I according to the present invention or 5-lipoxygenase activity for structurally related compounds are not disclosed.

U.S. Pat. No. 4,153,803 discloses cholesterol-lowering phenoxyalkanoic acid esters of the formula

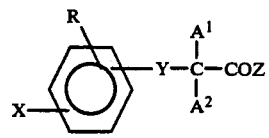

wherein, when Y is sulfur, X is hydrogen, benzyl, benzyloxy or benzylthio or substituted derivatives thereof; R is hydrogen, halogen, hydroxy, alkyl or alkoxy, $A^1$ and $A^2$ are hydrogen or alkyl and Z is amine or azacyclohydrocarbonyloxy.

SUMMARY OF THE INVENTION

The present invention relates to compounds of the Formula I

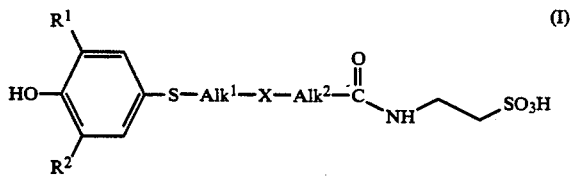

(I)

wherein $R^1$ and $R^2$ are the same or different and independently represent tert-alkyl, halogen, or phenyl; $Alk^1$ represents straight or branched chain alkylene of 2 to 10 carbon atoms which can optionally be 30 substituted by hydroxy, provided that said hydroxy is not attached to a carbon which is adjacent to sulfur or oxygen; X represents sulfur or oxygen; and $Alk^2$ represents straight or branched chain alkylene of 1 to 4 carbon atoms; and the pharmaceutically acceptable salts thereof. Compounds of the present invention are inhibitors of 5-lipoxygenase. Compounds of the present invention also inhibit superoxide generation.

The present invention also relates to methods for promoting anti-allergic, anti-inflammatory, and 5-lipoxygenase inhibiting effects in mammals in need thereof by the administration of preselected dosages of the compounds of the present invention or pharmaceutically acceptable salts thereof in appropriate non-toxic pharmaceutical dosage forms or compositions.

Another object of the present invention is to provide dosage unit forms adapted for, e.g., oral and/or parenteral administration and useful in the treatment, management and mitigation of allergies, inflammation and hypersensitivity reactions, psoriasis and related disorders and conditions in which physiologically active agents formed in the 5-lipoxygenase metabolic pathway are involved.

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," ANN INT. MED., 107:526–545 (1987) (see Table 1, p. 527) and Ward, P. A., et al., "Oxygen Radicals, Inflammation, and Tissue Injury," FREE RADICAL BIOLOGY & MEDICINE, 5:403–408 (1988). Among the clinical conditions in which oxygen radicals are thought to be involved are, for example, inflammatory-immune injury, autoimmune diseases, ischemia-reflow states, aging disorders, cancer cigarette-smoke effects, emphysema, acute respiratory distress syndrome (ARDS), atherosclerosis, rheumatoid arthritis, senile dementia, cataractogenesis, retinopathy of prematurity, radiation injury and contact dermatitiso Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells such as neutrophils, monocytes and macrophages, eosinophils, and endothelial cells; and antioxidation reactions; and exogenous, such as redox-cycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Those compounds of the present invention which inhibit superoxide generation may be useful in the treatment of diseases mediated by superoxide generation.

DETAILED DESCRIPTION OF THE INVENTION

The present invention also relates to compounds of the Formula II

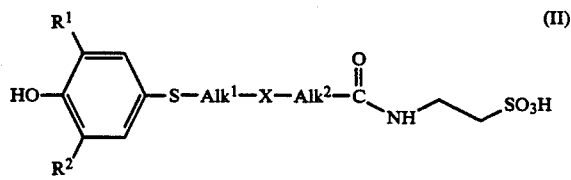

(II)

wherein $R^1$ and $R^2$ are the same or different and independently represent tert-butyl or phenyl; $Alk^1$ represents straight or branched chain alkylene of from 2 to 6 carbon atoms which can optionally be substituted by hydroxy, provided that said hydroxy is not attached to a carbon which is adjacent to sulfur or oxygen; X represents sulfur or oxygen; $Alk^2$ represents straight or branched chain alkylene of 1 to 4 carbon atoms; and the pharmaceutically acceptable salts thereof.

The present invention also relates to compounds of the formula III

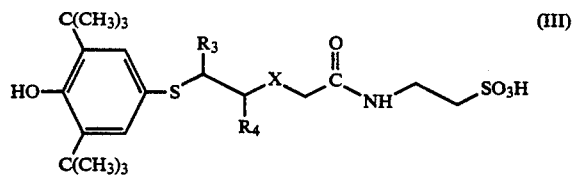

(III)

wherein $R^3$ and $R^4$ are alike or different and are hydrogen or alkyl of 1 to 4 carbon atoms, and X is sulfur or oxygen; and the pharmaceutically acceptable salts thereof.

Also preferred for use in the invention are compounds of the formula IV

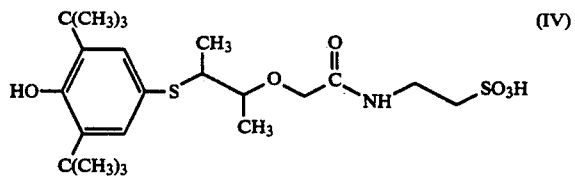

(IV)

and the pharmaceutically acceptable salts thereof.

The present invention includes stereoisomers and geometric isomers of the compounds of formula I. It will be appreciated by those skilled in the art that when $Alk_1$ or $Alk_2$ in formula I includes a substituted methylene radical, an asymmetric center exists and accordingly, d and l enantiomers or diastereomers and mixtures are obtained. The present invention includes such mixtures as well as the separate isomers.

The term "tert-alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Examples of such groups are tert-butyl, i.e., 1,1-dimethylethyl, 1-1-dimethylpropyl, 1-methyl-1-(ethyl)pentyl, 1,1-diethylpropyl, 1-ethyl-1-(propyl)butyl and the like.

The term "alkylene" refers to straight or branched chain alkylene groups having between about 1 to 10 carbon atoms including, for example, methylene, ethylene, propylene, 1-methylpropylene, butylene, 1,2-dimethylethylene, pentylene, 1-methylbutylene, isopentylene, neopentylene, hexylene, heptylene, octalene, etc.

The term "halogen" refers to chlorine, bromine, flourine, or iodine.

The expression "pharmaceutically acceptable salts" is intended to include those salts capable of being formed with the compounds of the present invention without materially altering the chemical structure thereof. Such salts include inorganic and organic cations or acid addition salts, such as sodium, potassium, calcium, ammonium, alkylammonium, triethanolamine, lysine, etc. well known to those skilled in the art. The foregoing salts are prepared in the conventional manner by neutralization of the compounds of Formula I with the desired base or acid.

The compounds of the present invention can be administered in such oral dosage forms as tablets, capsules, pills, powders, granules, elixirs, or syrups as well as aerosols for inhalation. Likewise, administration may be effected intravascularly, subcutaneously, intradermally, topically, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the particular condition. A dosage regimen can be effectively determined for each patient or animal by initial intravenous infusion at a low dosage level, e.g., 0.01 $\mu$g/kg/min and thereafter increasing the dosage until the desired effect is obtained. Thereafter, oral dosages can be determined which will yield equivalent blood levels of drug. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. In general, a unit dose form of the compounds of the invention will contain from about 1.75 to about 750 mg of compound. The compound may be administered in divided dosages, e.g., two or more times daily. The compounds may also be administered transdermally or topically to treat proliferative skin conditions such as psoriasis. The daily dosage may be administered in a single dose or in equal divided doses three or four times daily.

Unit dosage forms such as tablets and capsules can contain any suitable, predetermined, therapeutically effective amount of one or more active agent and a pharmaceutically acceptable carrier or diluent. Generally speaking, solid oral unit dosage forms of the compound of this invention will contain from 1.75 to 750 mg per tablet of drug as the effective lipoxygenase inhibiting amount of the compound.

In the case of acute allergic or hypersensitivity reactions, it is generally preferable to administer the initial dosage via the parenteral route and continue parenteral administration until the patient is stabilized, and can be maintained, if necessary, on oral dosing.

In the case of psoriasis and other skin conditions, it is preferred to apply a topical preparation of a compound of this invention to the affected area three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

When the compounds of this invention are co-administered with one or more cyclooxygenase inhibitors, they may conveniently be administered in a unit dosage form or may be administered separately. When the patient is allergic of hypersensitive to the cyclooxygenase inhibitor, it is preferred to initiate therapy with a compound of this invention prior to administration of the cyclooxygenase inhibitor.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

A typical tablet of this invention can have the following composition:

| Ingredient | Mg/Tablet |
| --- | --- |
| Active Ingredient | 100 |
| Starch U.S.P. | 57 |
| Lactose, U.S.P. | 73 |
| Talc, U.S.P. | 9 |

| Ingredient | Mg/Tablet |
|---|---|
| Stearic acid | 12 |

The compounds used in practicing the invention may be prepared as described in U.S. Pat. No. 4,711,903 and U.S. Pat. No. 4,755,524 both of which are incorporated herein by reference.

In addition, compounds of Formula I may be prepared as described in the following reaction Scheme A. In Scheme A, $R^1$, $R^2$, $Alk^1$, $Alk^2$, and X are defined as for Formula I above. The carboxylic acid (V) is reacted with oxalyl chloride in benzene followed by reaction with 2-aminoethane sulfonic acid in a stirring mixture of $K_2CO_3$ in tetrahydrofuran (THF). Protonation of the resulting potassium salt (VI) with an acid gives the taurine sulfonic acid (VII).

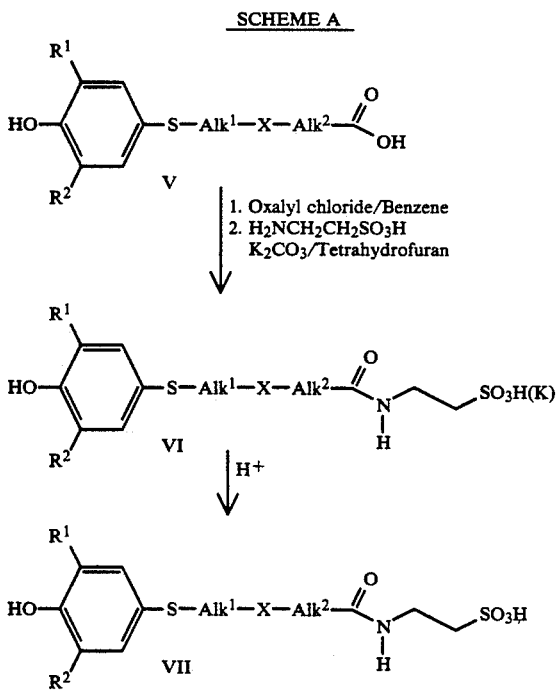

SCHEME A

BIOLOGICAL EVALUATIONS

The compounds of the invention are evaluated with respect to 5-lipoxygenase inhibition according to the following assay procedure.

Inhibition of 5-lipoxygenase, in vitro

The 100,000×g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca++ in the presence and absence of test compound. The product of 5-lipoxygenase, 5-hydroxyeicosa-tetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the $IC_{50}$ value (inhibitory concentration to inhibit 50%).

The compound of Example 5 inhibited 5-lipoxygenase with an average $IC_{50}$ of 3.25 $\mu$M in the above test.

The compounds of the invention are evaluated with respect to superoxide modulating activity according to the following assay procedure:

Human neutrophil superoxide generation

Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. *J. Biol. Chem.* 256:12640–12643, 1981.) To 5 million neutrophils in 2.85 ml of Krebs-Ringer phosphate buffer, pH 7.2, 50 ul of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading minus the initial reading (before addition of FMLP) was used to calculate nanomoles of superoxide generated based on a molar extinction coefficient of $2.1 \times 10^4$ cm$^{-1}$mole$^{-1}$.

Isolation of human neutrophils

Human neutrophils were isolated from freshly drawn blood of healthy donors. Two ml of 5% dextran (MW 200,000–300,000) in saline was added to 10 ml aliquots of blood, mixed and placed upright for 45 min. at 37° C. Approx. 8–10 ml of the plasma-white cell suspension from the dextran sedimentation was layered on 3 ml of Ficol-paque in a 15 ml tube and centrifuged at 400 g for 30 min. The supernate, containing plasma and platelets, was discarded by aspiration, and the pellet, containing predominantly neutrophils, was resuspended in 1 ml saline. The suspension was transferred to a clean tube, and pooled with other aliquots of blood treated similarly. The pooled suspension was centrifuged at 350 g for 5 min. and supernate discarded. The pellet was resuspended in 5 ml of 0.05% NaCl with a plastic Pasteur pipette for 25 seconds to lyse contaminating red cells, then 5 ml of 1.75% NaCl added to regain isotonicity. The red cell lysing procedure was repeated, the cells suspended in appropriate buffer (depending on assay) and counted.

The compound of Example 5 inhibited superoxide generation with an average $IC_{50}$ of 87.5 $\mu$M in the above test.

The compounds of the present invention can be prepared from readily available starting materials.

The carboxylic acid starting materials used to make the compounds of the present invention can be prepared as disclosed in U.S. Pat. No. 4,711,903; U.S. Pat. No. 4,755,524; U.S. Pat. No. 5,019,597; and U.S. Pat. No. 5,064,806, all of which are incorporated herein by reference.

The following non-limiting examples further illustrate details for the preparation of the compounds used in practicing the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus or by differential scanning calorimetry (DSC) and are uncorrected.

EXAMPLE 1

3,5-bis(1,1-dimethylethyl)-4-hydroxyphenyl thiocyanate

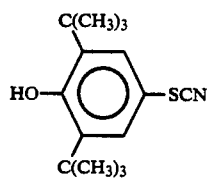

To a three-necked, round bottom 5 L flask, equipped with a mechanical stirrer, gas inlet, thermometer and gas outlet, was added 2,6-di-tert-butylphenol (474 g, 2.30 mole), ammonium thiocyanate (76.12 g, 4.83 mole) and methanol (1200 mL). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1 and ½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from 5 pentane and dried in vacuo to yield the product as a white powder, m.p. 61.5°–63° C.

Analysis calc. for $C_{15}H_{21}NSO$:

Theory: C, 68.40; H, 8.03; N, 5.32; S, 12.17.
Found: C, 68.85; H, 8.05; N, 5.29; S, 12.12.

EXAMPLE 2

2,6-bis(1,1-dimethylethyl)-4-mercaptophenol

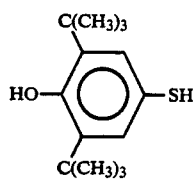

3,5-bis(1,1-dimethylethyl)-4-hydroxyphenyl thiocyanate (55 g, 0.209 mole) was dissolved in acetone (200 mL) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

(±)2,6-bis(1,1-dimethylethyl)-4-[(2S\*-hydroxy-1R\*-methylpropyl)thio]phenol

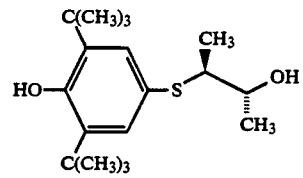

An argon-purged vessel was charged with 54 L of anhydrous methanol which was then purged with argon for 5 min. About 12 L of methanol was distilled off at atmospheric pressure, and the remaining methanol was transferred to pressure cans under argon. The dry, argon-purged vessel was charged with 3.03 kg of sodium methoxide followed by 29.7 kg of methanol from the pressure cans. The mixture was stirred for 10 min, and 6.7 kg of 2,6-bis(1,1- dimethylethyl)-4-mercaptophenol was added in small portions under argon. The mixture was stirred for 1 h at room temperature and cooled to 0° C. at which point 2.23 kg of trans-2,3-epoxybutane was added followed by a 2.7 kg methanol rinse. The mixture was stirred at 0° C. for 4 h and then at less than 25° C. for 16 h. When the reaction was complete as indicated by thin layer chromatography, the reaction mixture was added to 59 L of 1 N hydrochloric acid, and the aqueous solution was extracted twice with a total of 89 L of ethyl acetate. The combined organic phase was washed once with 34 L of dilute aqueous sodium chloride solution and once with 13 L of saturated aqueous sodium chloride solution. The organic phase was dried over 3.5 kg of anhydrous magnesium sulfate and filtered. The solvent was removed by distillation under reduced pressure. The crude product was dissolved in 6.7 L of refluxing n-hexane, and the solution was cooled to 5° C. The solid was collected by filtration, washed with cold (about 0° C.) n-hexane and dried at 50° C. in a vacuum oven to give 7.44 kg ( 85% of theory) of (+) 2,6-bis (1,1-dimethylethyl)-4-[(2S\*-hydroxy-1R\*-methylpropyl) thio]phenol.

EXAMPLE 4

(÷)
(±)[2S\*-[[3,5-bis(1-dimethylethyl)-4-hydroxyphenyl]thio]-1R\*-methylpropopyl]acetic acid

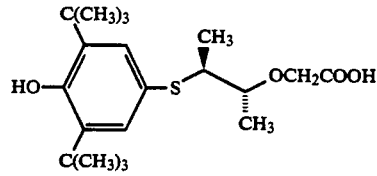

A dry, argon purged vessel was charged with 1.6 kg of sodium hydride (60% dispersion in oil) which was then washed three times with a total of 21 kg of n-heptane. The reaction vessel was cooled to −20° C., and 41 L of dry tetrahydrofuran (THF) was added under argon. A solution of 4.0 kg of (±) (2,6)-bis(1,1-dimethylethyl)-4-[(2S\*-hydroxy-1R\*-methylpropyl)-thio]phenol in 16 L of tetrahydrofuran was added slowly to the sodium hydride suspension, and the mixture was warmed to 0°–5° C. and stirred for 1.5 h. The tetrahydrofuran was removed at reduced pressure, and 12 L of dimethyl sulfoxide was added under argon. A solution of 1.9 kg of sodium chloroacetate in 40 L of dimethyl sulfoxide was added, and the mixture was stirred at room temperature for approximately 15 h. When the reaction was complete, as indicated by thin layer chromatography, the reaction mixture was added to approximately 178 L of water at 5°–10° C., and the aqueous solution was extracted twice with a total of 60 L of n-heptane. The aqueous phase was acidified with 14 L of 4 N hydrochloric acid and extracted three times with a total of 95 L of ethyl acetate. The combined organic phase was washed twice with a total of 74 L of water and once with 20 L of saturated aqueous sodium chloride solution. The organic phase was dried over 2.0 kg of anhydrous magnesium sulfate, filtered, and the solvent was removed by distillation under reduced pressure. The product was dissolved in 40 L of refluxing n-hexane, and the solution was cooled to room temperature. The product was collected by filtration, washed twice with a total of 20 L of n-hexane and dried at room temperature in a vacuum oven to give 4.27 kg (90% of theory) of (±)[2S*-[[3,5-bis(1,1-dimethyl-ethyl)-4-hydroxyphenyl]thio]-1R*-methylpropoxy]acetic acid (first crop). The hexane filtrate was concentrated under vacuum to give an additional 0.23 kg of product (4.80% of theory).

EXAMPLE 5

2-[[[[2S*-[[3,5-bis(1,1-dimethylethyl)-4-hydroxyphenyl]-thio]-1R*-methylpropoxy]acetyl]amino]ethanesulfonic acid, potassium salt

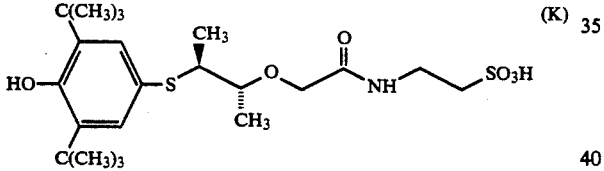

Oxalyl chloride (0.41 g, 0.0033 mole) was added to a solution of (±) [2S*-[[3,5-bis(1-dimethylethyl)-4-hydroxyphenyl]thio]-1R*-methyl-propoxy]acetic acid (1.0 g, 0.0027 mole) in benzene (100 mL). The reaction was stirred at room temperature for 6 hours and was concentrated to an oil. The oil was redissolved in benzene (50 mL) and concentrated once more. Tetrahydrofuran (250 mL), potassium carbonate (1.1 g, 0.0081 mole) and 2-aminoethane sulfonic acid (0.34 g, 0.0027 mole) was added and the mixture was stirred at room temperature for 6 days, heated to 50° C. for 4 days and at room temperature for 7 days. The mixture was filtered and the filtrate was concentrated to an oil. The product was purified by silica gel chromatography as the potassium salt. The structure was confirmed by NMR, IR, mass spectroscopy and elemental analysis.

Analysis calculated for: $C_{22}H_{36}NO_6S_2K\cdot H_2O$:
Theory: C, 49,69; H, 7.20; N, 2.63.
Found: C, 49,52; H, 7.12; N, 2.52.

EXAMPLES 6 TO 19

Starting with the A compound in Table 1 and following the procedure of Example 5 gives the corresponding B taurine conjugate shown in Table 2.

TABLE 1

| Ex 6A | [[2-[[3,5-bis(1,1-dimethylethyl)-4-hydroxyphenyl]thio]ethyl]thio]acetic acid |

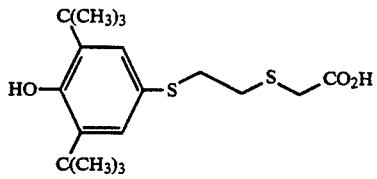

| Ex 7A | 3-[[2-[[3,5-bis(1,1-dimethylethyl)-4-hydroxyphenyl]thio]ethyl]thio]propanoic acid |

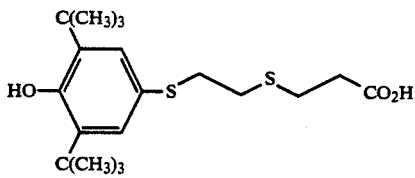

| Ex 8A | 4-[[2-[[3,5-bis(1,1-dimethylethyl)-4-hydroxyphenyl]thio]ethyl]thio]butanoic acid |

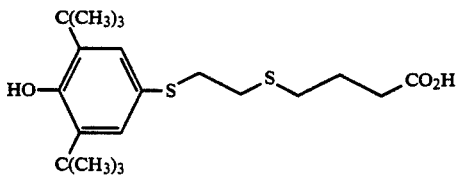

| Ex 9A | [[2-[[3,5-bis(1,1-dimethylethyl)-4-hydroxyphenyl]thio]-1-methylpropyl]thio]acetic acid |

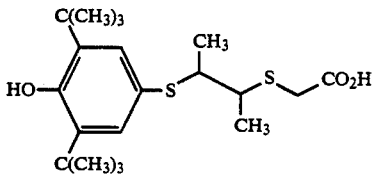

| Ex 10A | [[2-[[3,5-bis(1,1-dimethylethyl)-4-hydroxyphenyl]thio]ethoxy]acetic acid |

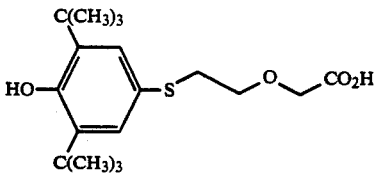

| Ex 11A | [[3-[[3,5-bis(1,1-dimethylethyl)-4-hydroxyphenyl]thio]-2-hydroxypropyl]thio]acetic acid |

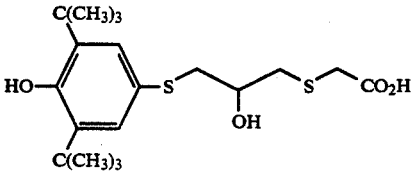

| Ex 12A | [2R*-[[3,5-bis(1,1-dimethylethyl)-4-hydroxyphenyl]thio]-1R*-methylpropoxy]acetic acid |

TABLE 1-continued

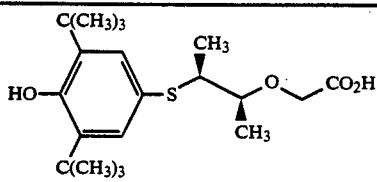

Ex 13A [[4-[[3,5-bis(1,1-dimethylethyl)-4-hydroxyphenyl]thio]butyl]thio]acetic acid

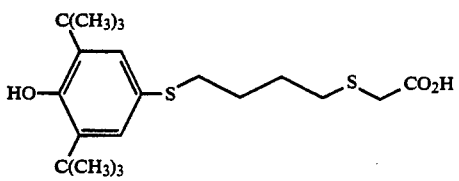

Ex 14A (−) Enantiomer: (−)[2S*-[[3,5-bis(1,1-dimethylethyl)-4-hydroxyphenyl]thio]-1R*-methylpropoxy]acetic acid

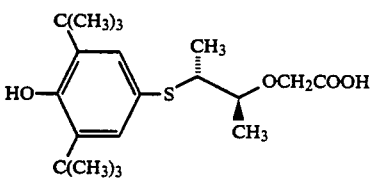

OR

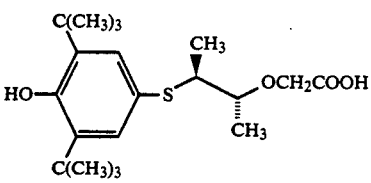

Ex 15A (+) Enantiomer: (+)[2S*-[[3,5-bis(1,1-dimethylethyl)-4-hydroxyphenyl]thio]-1R*-methylpropoxy]acetic acid TABLE 1-continued

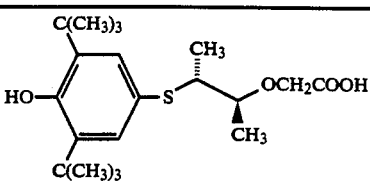

OR

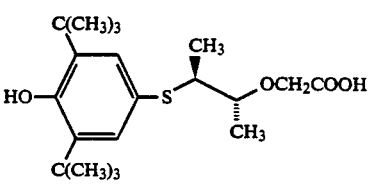

Ex 16A [[2-[(2'-hydroxy[1,1':3',1''-terphenyl]-5'-yl)thio]ethyl]thio]acetic acid

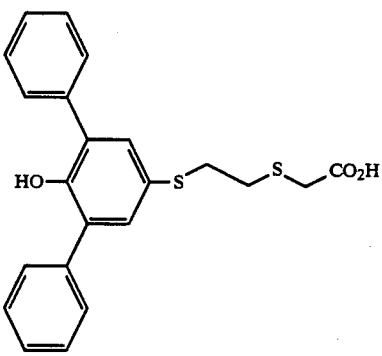

Ex 17A Starting with 3,5-dichloro-4-mercaptophenol and following the procedure described in Example 31 of the U.S. 4,755,524 incorporated herein by reference gives [2-[(3,5-dichloro-4-hydrophenyl)thio]ethoxy]acetic acid.

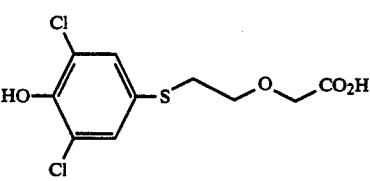

TABLE 2

Ex 6B  2-[[[[2-[[3,5-bis(1,1-dimethylethyl)-4-hydroxyphenyl]thio]ethyl]acetyl]amino]ethanesulfonic acid, potassium salt

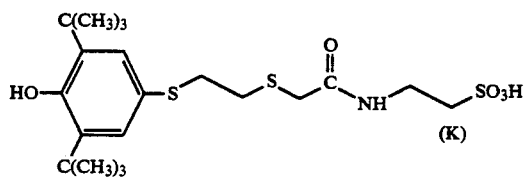

Ex 7B  2-[[3-[[2-[[3,5-bis(1,1-dimethylethyl)-4-hydroxyphenyl]thio]ethyl]thio]propanoyl]amino]ethanesulfonic acid, potassium salt

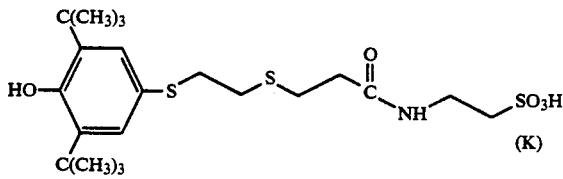

TABLE 2-continued

Ex 8B  2-[[4-[[2-[[3,5-bis(1,1-dimethylethyl)-4-hydroxyphenyl]thio]ethyl]thio]butanoyl]amino]ethanesulfonic acid, potassium salt

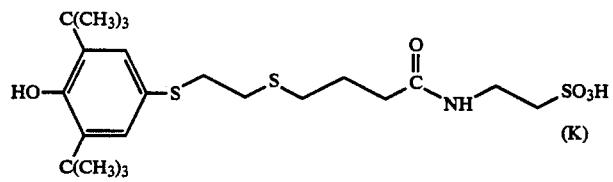

Ex 9B  2-[[[[2-[[3,5-bis(1,1-dimethylethyl)-4-hydroxyphenyl]thio]-1-methylpropyl]thio]acetyl]amino]ethanesulfonic acid, potassium salt

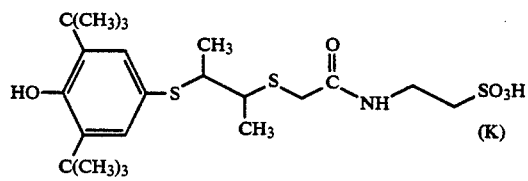

Ex 10B  2-[[[2-[[3,5-bis(1,1-dimethylethyl)-4-hydroxyphenyl]thio]ethoxy]acetyl]amino]ethanesulfonic acid, potassium salt

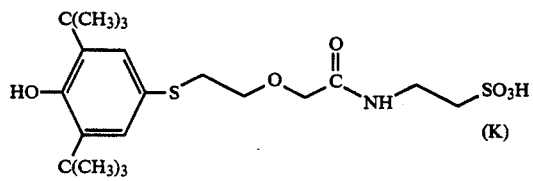

Ex 11B  2-[[[[3-[[3,5-bis(1,1-dimethylethyl)-4-hydroxyphenyl]thio]-2-hydroxypropyl]thio]acetyl]amino]ethanesulfonic acid, potassium salt

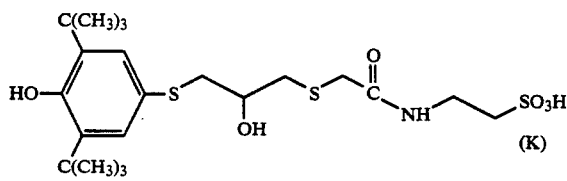

Ex 12B  2-[[[2R*-[[3,5-bis(1,1-dimethylethyl)-4-hydroxyphenyl]thio]-1R*-methylpropoxy]acetyl]amino]ethanesulfonic acid, potassium salt

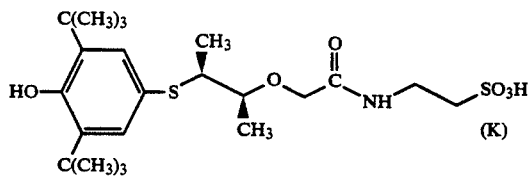

Ex 13B  2-[[[[4-[[3,5-bis(1,1-dimethylethyl)-4-hydroxyphenyl]thio]butyl]thio]acetyl]amino]ethanesulfonic acid, potassium salt

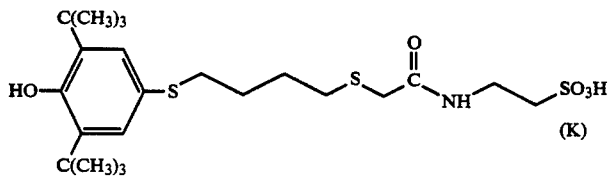

Ex 14B  (−) Enantiomer: (−)2-[[[2S*-[[3,5-bis(1,1-dimethylethyl)-4-hydroxyphenyl]thio]-1R*-methylpropoxy]acetyl]acid]ethanesulfonic acid, potassium salt

TABLE 2-continued

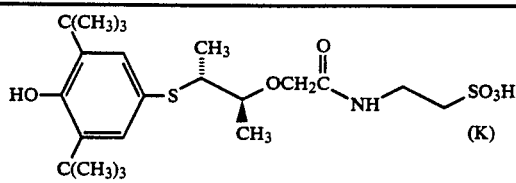
(K)

OR

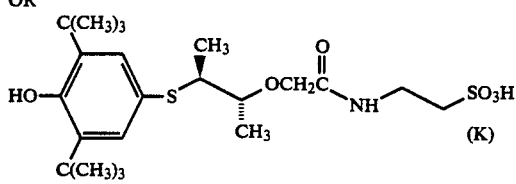
(K)

Ex 15B (+) Enantiomer: (+)2-[[[2S*-[[3,5-bis(1,1-dimethylethyl)-4-hydroxyphenyl]thio]-1R*-methylpropoxy]acetyl]acid]ethanesulfonic acid, potassium salt

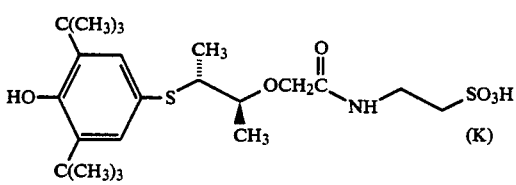
(K)

OR

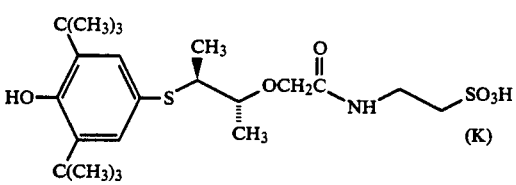
(K)

Ex 16B 2-[[[[2-[(2'-hydroxy[1,1':3',1''-terphenyl]-5'-yl)thio]ethyl]thio]acetyl]amino]ethanesulfonic acid, potassium salt

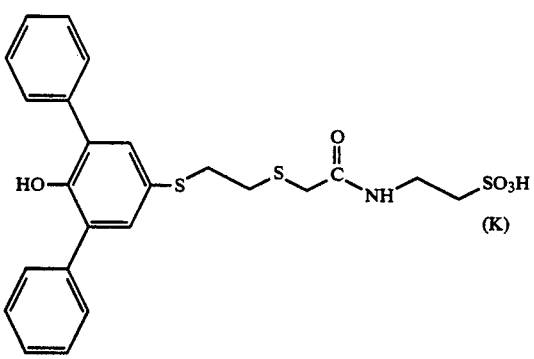
(K)

Ex 17B 2-[[[2-[(3,5-dichloro-4-hydroxyphenyl)thio]-ethoxy]acetyl]amino]ethanesulfonic acid, potassium salt.

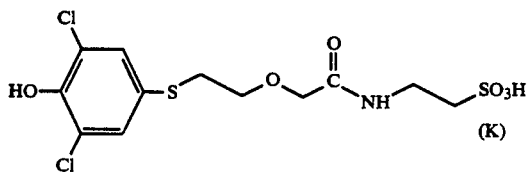
(K)

What is claimed is:
1. A compound of the formula I

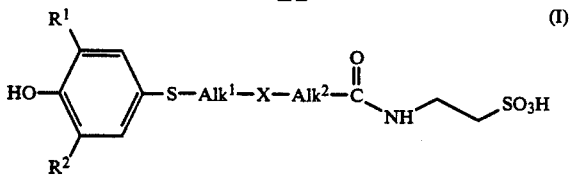

wherein R¹ and R² are the same or different and independently represent tert-alkyl, halogen, or phenyl; Alk¹ represents straight or branched chain alkylene of 2 to 10 carbon atoms which can optionally be substituted by hydroxy, provided that said hydroxy is not attached to a carbon which is adjacent to sulfur or oxygen, X represents sulfur or oxygen, and Alk² represents straight or branched chain alkylene of 1 to 4 carbon atoms; or a pharmaceutically acceptable salt thereof.

2. A compound according to claim 1 of the formula II

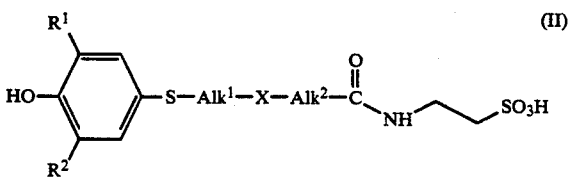

wherein R¹ and R² are the same or different and independently represent tert-butyl or phenyl; Alk¹ represents straight or branched chain alkylene of from 2 to 6 carbon atoms which can optionally be substituted by hydroxy, provided that said hydroxy is not attached to a carbon which is adjacent to sulfur or oxygen, X represents sulfur or oxygen, Alk² represents straight or branched chain alkylene of 1 to 4 carbon atoms; or a pharmaceutically acceptable salt thereof.

3. A compound according to claim 2 of the formula III

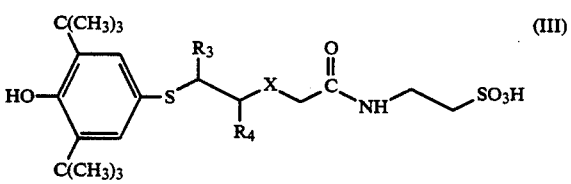

wherein R³ and R⁴ are alike or different and are hydrogen or alkyl of 1 to 4 carbon atoms, and X is sulfur or oxygen; or a pharmaceutically acceptable salt thereof.

4. A compound according to claim 3 of the formula IV

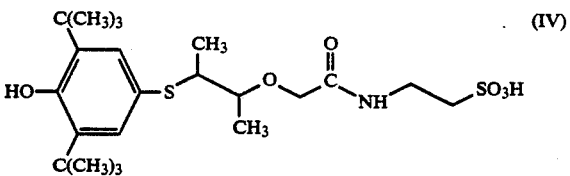

or a pharmaceutically acceptable salt thereof.

5. A compound according to claim 4 which is 2-[[[2S*-[[3,5-bis (1,1-dimethylethyl)-4-hydroxyphenyl]-thio]-1R,-methylpropoxy]-acetyl]amino]ethanesulfonic acid.

6. A compound according to claim 4 which is 2-[[[2S*-[[3,5-bis(1,1-dimethylethyl)-4-hydroxyphenyl]-thio]-1R*-methylpropoxy]-acetyl]amino]ethanesulfonic acid, potassium salt.

7. A pharmaceutical composition for use in the treatment of Lipoxygenase mediated conditions and/or inflammation and allergy which comprises a therapeutically effective amount of a compound of the formula I

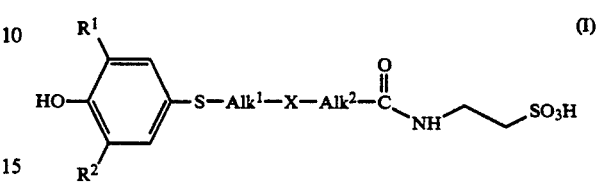

wherein R¹ and R² are the same or different and independently represent tert-alkyl, halogen, or phenyl; Alk¹ represents straight or branched chain alkylene of 2 to 10 carbon atoms which can optionally be substituted by hydroxy, provided that said hydroxy is not attached to a carbon which is adjacent to sulfur or oxygen, X represents sulfur or oxygen, and Alk² represents straight or branched chain alkylene of 1 to 4 carbon atoms; or a pharmaceutically acceptable salt thereof; and a pharmaceutically acceptable carrier.

8. A pharmaceutical composition according to claim 7 which comprises a therapeutically effective amount of a compound of the formula II

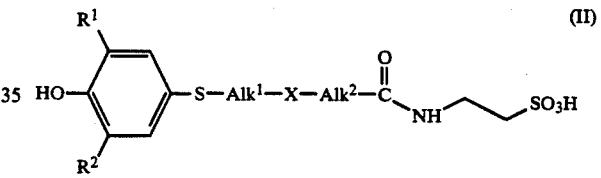

wherein R¹ and R² are the same or different and independently represent tert-butyl, or phenyl; Alk¹ represents straight or branched chain alkylene of from 2 to 6 carbon atoms which can optionally be substituted by hydroxy, provided that said hydroxy is not attached to a carbon which is adjacent to sulfur or oxygen, X represents sulfur or oxygen, Alk² represents straight or branched chain alkylene of 1 to 4 carbon atoms; or a pharmaceutically acceptable salt thereof; and a pharmaceutically acceptable carrier.

9. A pharmaceutical composition according to claim 8 which comprises a therapeutically effective amount of a compound of the formula III

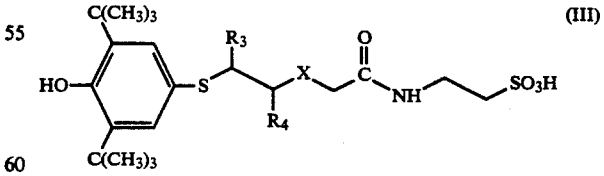

wherein R³ and R⁴ are alike or different and are hydrogen or alkyl of 1 to 4 carbon atoms, and X is sulfur or oxygen; or a pharmaceutically acceptable salt thereof; and a pharmaceutically acceptable carrier.

10. A pharmaceutical composition according to claim 9 which comprises a therapeutically effective amount of a compound of the formula IV

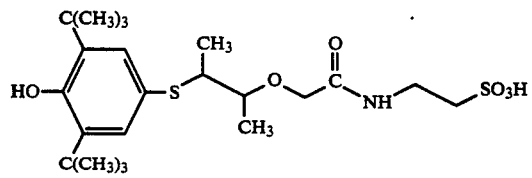

(IV)

or a pharmaceutically acceptable salt thereof; and a pharmaceutically acceptable carrier.

11. A pharmaceutical composition according to claim 10 which comprises a therapeutically effective amount of 2-[[[2S*-[[3,5-bis(1,1-dimethylethyl)-4-hydroxyphenyl]thio]-1R*-methylpropoxy]-acetyl]amino]ethanesulfonic acid; and a pharmaceutically acceptable carrier.

12. A pharmaceutical composition which comprises a therapeutically effective amount of 2-[[[2S*-[[3,5-bis(1,1-dimethylethyl)-4-hydroxyphenyl]thio]-1R*-methylpropoxy] -acetyl]amino]ethanesulfonic acid, potassium salt; and a pharmaceutically acceptable carrier.

* * * * *

UNITED STATES PATENT AND TRADEMARK OFFICE
CERTIFICATE OF CORRECTION

PATENT NO. : 5,326,907

DATED : July 5, 1994

INVENTOR(S) : Partis, et al.

Page 1 of 2

It is certified that error appears in the above-indentified patent and that said Letters Patent is hereby corrected as shown below:

Column 5, line 13, reading "30 substituted by" should read -- substituted by --.

Column 5, line 42, reading "ANN INT." should read -- ANN. INT. --.

Column 5, line 49&50, reading "cancer cigarette-smoke" should read -- cancer, cigarette-smoke --.

Column 5, line 53, reading "contact dermatitiso" should read -- contact dermatitis. --.

Column 11, line 35, reading "from 5 pentane" should read -- from pentane --.

Column 12, line 42, reading "of (+)" should read -- of (±) --.

Column 12, line 47, reading "EXAMPLE 4 (÷)" should read -- EXAMPLE 4 --.

Column 12, line 49, reading "methylpropopyl]" should read -- methylpropoxy] --.

Column 14, line 44, reading "Ex 10A [[2-[[3,5-bis" should read -- Ex 10A [2-[[3,5-bis --.

Column 16, line 50, reading "thio]ethyl]acetyl]" should read -- thio]ethyl]thio]acetyl] --.

Column 19, line 20, reading "acetyl]acid]" should read -- acetyl]amino] --.

UNITED STATES PATENT AND TRADEMARK OFFICE
CERTIFICATE OF CORRECTION

PATENT NO. : 5,326,907
DATED : July 5, 1994
INVENTOR(S) : Partis, et al.

It is certified that error appears in the above-indentified patent and that said Letters Patent is hereby corrected as shown below:

Column 21, line 65, reading "1R,-methylpropoxy" should read -- 1R*-methylpropoxy --.

Column 22, line 4, reading "Lipoxygenase" should read -- lipoxygenase --.

Signed and Sealed this

Twenty-ninth Day of November, 1994

Attest:

BRUCE LEHMAN

Attesting Officer

Commissioner of Patents and Trademarks